US00RE35811E

United States Patent [19]

Shiokawa et al.

[11] E Patent Number: Re. 35,811

[45] Reissued Date of Patent: May 26, 1998

[54] INSECTICIDALLY ACTIVE NITRO GUANIDINE COMPOUNDS

[75] Inventors: Kozo Shiokawa, Kanagawa-ken; Shinichi Tsuboi, Tokyo; Koichi Moriya, Tochigi; Yumi Hattori, Ibaraki; Ikuro Honda, Tokyo; Katsuhiko Shibuya, Tochigi, all of Japan

[73] Assignee: Nihon Bayer Agrochem K.K., Tokyo, Japan

[21] Appl. No.: 538,756

[22] Filed: Oct. 3, 1995

Related U.S. Patent Documents

Reissue of:

[64] Patent No.: 5,051,434
Issued: Sep. 24, 1991
Appl. No.: 438,543
Filed: Nov. 16, 1989

[30] Foreign Application Priority Data

Nov. 29, 1988 [JP] Japan ..... 63-299419
Feb. 13, 1989 [JP] Japan ..... 1-031145

[51] Int. Cl.[6] ..... C07D 213/38; A01N 43/40

[52] U.S. Cl. ..... 514/357; 544/334; 544/335; 546/331; 546/332; 548/100; 548/205; 548/125; 548/127; 548/247; 514/256; 514/361; 514/365; 514/378

[58] Field of Search ..... 546/331, 332; 544/334, 335; 548/100, 205, 247, 125, 127; 514/256, 357, 361, 365, 378

[56] References Cited

U.S. PATENT DOCUMENTS 3,457,188 7/1969 Niemers et al. ..... 514/332
4,499,097 2/1985 Tomcufcik et al. ..... 514/341

FOREIGN PATENT DOCUMENTS 0302389 2/1989 European Pat. Off. .
302833 2/1989 European Pat. Off. ..... 546/331
303570 2/1989 European Pat. Off. ..... 546/303
234064 10/1987 Japan ..... 546/303
233903 9/1988 Japan ..... 546/303
2201596 2/1988 United Kingdom ..... 546/303

OTHER PUBLICATIONS

Nihon Kagaku Zasshi, vol. 83, No. 2, pp. 218–222, 1962.

Bulletin of National Institute of Hygienic Sciences, No. 88, 1970, "Screening Test on Anticancer and . . . ", Kamiya and Koshinuma, et al.

Bulletin of National Institute of Hygienic Sciences, No. 102, 1984, "Sunthesis of 3–Nitro–1–nitroso . . . ", Kamiya and Koshinuma, et al.

*Primary Examiner*—Zinna Northington Davis
*Attorney, Agent, or Firm*—Sprung Kramer Schaefer & Briscoe

[57] ABSTRACT

Insecticidal novel nitro compounds of the formula

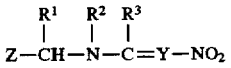

in which $R^1$ and $R^2$ are hydrogen or $C_{1-4}$ alkyl, $R^3$ is —S—$R^4$ or

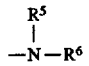

in which $R^4$ is $C_{1-4}$ alkyl, $R^5$ and $R^6$ are hydrogen or $C_{1-4}$ alkyl, Y is CH or N, and Z is a five- or six-membered heterocyclic group having at least one nitrogen atom which may be substituted by halogen or $C_{1-4}$ alkyl, provided that where Y is CH, then $R^1$ is $C_{1-4}$ alkyl.

19 Claims, No Drawings

INSECTICIDALLY ACTIVE NITRO GUANIDINE COMPOUNDS

Matter enclosed in heavy brackets [ ] appears in the original patent but forms no part of this reissue specification; matter printed in italics indicates the additions made by reissue.

*This application is a Reissue of 07/438,543 filed Nov. 16, 1989, U.S. Pat. No. 5,051,434.*

The present invention relates to novel nitro compounds, to process for their preparation and to their use as insecticides.

It has already been disclosed that a certain group of 2-nitro-1,1-ethenediamines is useful as medicaments which influence the circulation, in particular as hypotensive agents (see U.S. Pat. No. 4,567,188), a certain group of N-cyanoisothioureas is useful as medicaments for treating ulcers (see Japanese Patent Laid-open No. 234,064/1987), the N-cyanoisothioureas disclosed in such Japanese patent application have also controlling insects and plant-destructive nematodes (see Japanese Patent Laid-open No. 233,903 and EP-A 303,570), and a certain group of α-unsaturated amines having insecticidal/miticidal activity (see EP-A 0302389).

There have now been found novel nitro compounds of the formula (I)

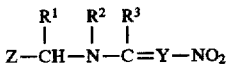

(I)

wherein $R^1$ and $R^2$ are hydrogen or $C_{1-4}$ alkyl, $R^3$ is —S—$R^4$ or

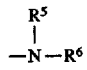

in which $R^4$ is $C_{1-4}$ alkyl, $R^5$ and $R^6$ are hydrogen or $C_{1-4}$ alkyl, Y is CH or N, and Z is a five- or six-membered heterocyclic group having at least one nitrogen atom which may be substituted by halogen or $C_{1-4}$ alkyl, provided that where Y is CH, then $R^1$ is $C_{1-4}$ alkyl.

The compounds of the formula (I) can be obtained by a process in which a) (in the case where $R^3$ is —S—$R^4$ and Y is CH, then $R^1$ is replaced by $R^7$, in which $R^7$ is $C_{1-4}$ alkyl) compounds of the formula (II)

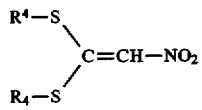

(II)

wherein $R^4$ has the same meaning as mentioned above, are reacted with compounds of the formula (III)

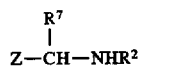

(III)

wherein $R^7$, $R^2$ and Z have the same meanings as mentioned above, in the presence of inert solvents, b) (in the case where $R^3$ is

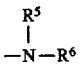

and Y is CH, then $R^1$ is replaced by $R^7$) compounds of the formula (Ia)

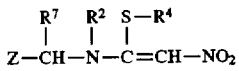

(Ia)

wherein $R^7$, $R^2$, $R^4$ and Z have the same meanings as mentioned above, are reacted with compounds of the formula (IV)

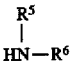

(IV)

wherein $R^5$ and $R^6$ have the same meanings as mentioned above, in the presence of inert solvents, or c) (in the case where $R^3$ is —S—$R^4$ and Y is N) compounds of the formula (V)

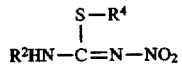

(V)

wherein $R^2$ and $R^4$ have the same meanings as mentioned above, are reacted with compounds of the formula (VI)

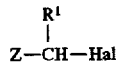

(VI)

wherein $R^1$ and Z have the same meanings as mentioned above, and Hal represents halogen atom, in the presence of inert solvents, and if appropriate in the presence of acid binders, or d) (in the case where $R^3$ is

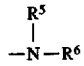

and Y is N) compounds of the formula (Ic)

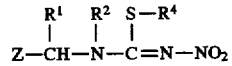

(Ic)

wherein $R^1$, $R^2$, $R^4$ and Z have the same meanings as mentioned above, are reacted with the above compounds of the formula (IV), in the presence of inert solvents.

The novel nitro compounds exhibit powerful insecticidal properties.

Surprisingly, the nitro compounds according to the invention exhibit a substantially greater insecticidal action than those known from the above-cited prior art.

In the formulae, the $C_{1-4}$ alkyl groups $R^1$, $R^2$, $R^4$, $R^5$ and $R^6$ are straight-chain or branched, such as methyl, ethyl, n- and i-propyl and n-, i-, s- and t-butyl. Methyl is preferred.

In the formulae, the five- or six-membered heterocyclic group Z contains at least one nitrogen atom as a ring member. Preferred are 3-pyridyl, 4-pyridyl and 5-thiazolyl, particularly preferred are 3-pyridyl and 5-thiazolyl.

The substituent halogen atoms on the five- or six-membered heterocyclic group Z are fluorine, chlorine, bromine and iodine. Preferred is chlorine.

The substituent $C_{1-4}$ alkyl groups on the five- or six-membered heterocyclic group Z are straight-chain or branched, such as methyl, ethyl, n- and i-propyl and n-, i-, s- and t-butyl. Preferred is methyl.

The substituent may be in all possible positions of the five- or six-membered heterocyclic group Z.

Preferably it is in the 6 position of the 3-pyridyl ring and in the 2 position of the 5-thiazolyl ring.

Among the nitro compounds according to the invention of the formula (I), preferred compounds are those in which $R^1$ and $R^2$ are hydrogen or methyl, $R^3$ is —S—$R^4$ or

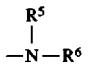

in which $R^4$ is methyl, $R^5$ and $R^6$ are hydrogen or methyl,

Y is CH or N, and

Z is 3-pyridyl, 4-pyridyl or 5-thiazolyl which may be substituted by chlorine or methyl, provided that where Y is CH, then $R^1$ is methyl.

More preferred nitro compounds of the formula (I) are those
in which $R^1$ and $R^2$ are hydrogen or methyl, $R^3$ is

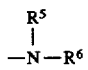

in which $R^5$ and $R^6$ are hydrogen or methyl,

Y is CH or N, and

Z is 2-chloro-5-pyridyl or 2-chloro-5-thiazolyl, provided that where Y is CH, then $R^1$ is methyl.

Much more preferred nitro compounds of the formula (I) are those
in which $R^1$ and $R^2$ are hydrogen or methyl, $R^3$ is

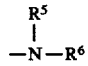

in which $R^5$ and $R^6$ are hydrogen or methyl,

Y is CH or N, and

Z is 2-chloro-5-pyridyl or 2-chloro-5-thiazolyl, provided that where Y is

CH then $R^1$ is methyl, or where $R^2$ is hydrogen and $R^3$ is —$NHCH_3$ then Y is N.

Very particularly preferred nitro compounds of the formula (I) are those
in which $R^1$ and $R^2$ are hydrogen or methyl, $R^3$ is

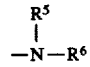

in which $R^5$ and $R^6$ are hydrogen or methyl,

Y is N, and

Z is 2-chloro-5-pyridyl.

Specifically, the following compounds may be mentioned:

3-(2-chloro-5-pyridylmethyl)-1-methyl-2-nitroguanidine, 3-(2-chloro-5-pyridylmethyl)-1,1-dimethyl-2-nitroguanidine, 3-(2-chloro-5-pyridylmethyl)-1,3-dimethyl-2-nitroguanidine, 3-(2-chloro-5-pyridylmethyl)-1,1,3-trimethyl-2-nitroguanidine, 3-(2-chloro-5-pyridylmethyl)-3-methyl-2-nitroguanidine, 3-(2-chloro-5-thiazolylmethyl)-1-methyl-2-nitroguanidine, 1-[1-(2-chloro-5-pyridyl)ethylamino]-1-dimethylamino-2-nitroethylene, 1-amino-1-[1-(2-chloro-5-pyridyl)ethylamino]-2-nitroethylene, 1-[1-(2-chloro-5-pyridyl)ethylamino]-1-methylamino-2-nitroethylene, and 1-{N-[1-(2-chloro-5-pyridyl)ethyl]-N-methylamino}-1-dimethylamino-2-nitroethylene.

If, for example, in the above process a), 1,1-bis-methylthio-2-nitroethylene and 1-(2-chloro-5-pyridyl) ethylamine are used as starting materials, the course of the reaction can be represented by the following equation:

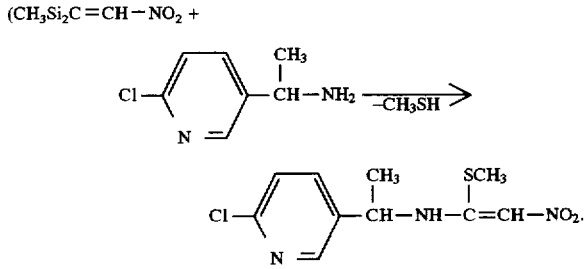

If, for example, in the above process b), 1-[1-(2-chloro-5-pyridyl)ethylamino]-1-methylthio-2-nitroethylene and methylamine are used as starting materials, the course of the reaction can be represented by the following equation:

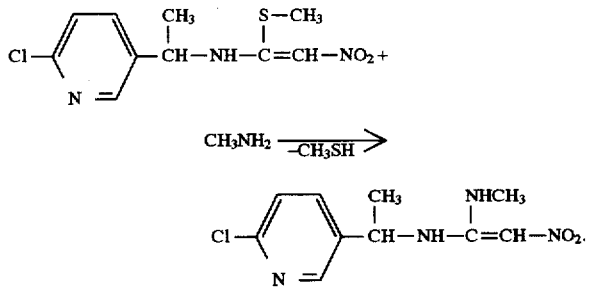

If, for example, in the above process c), 2-methyl-3-nitroisothiourea and 2-chloro-5-chloromethylpyridine are used as starting materials, the course of the reaction can be represented by the following equation:

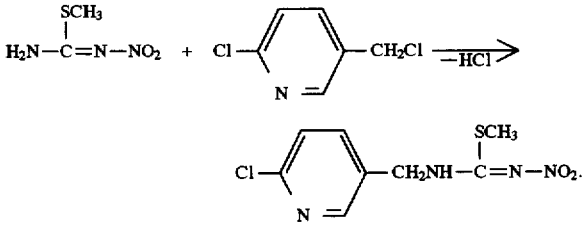

If, for example, in the above process d), 1-(2-chloro-5-pyridylmethyl)-3-nitro-2-methylisothiourea and dimethylamine are used as starting materials, the course of the reaction can be represented by the following equation:

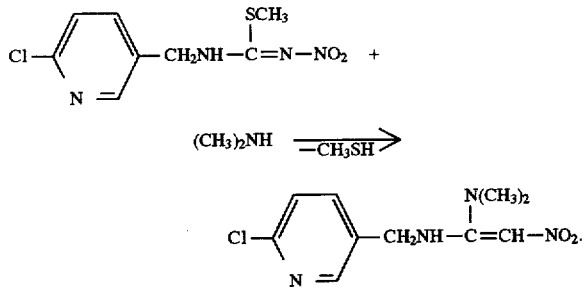

In the process a), the compounds of the formula (II) as starting materials mean those based on the aforementioned definition of $R^4$.

In the formula (II), $R^4$ preferably has the meaning already given above.

The compounds of the formula (II) include known compounds (see e.g. Chem. Ber., vol. 100, pages 591–604, 1967) and, as an example, 1,1-bis-methylthio-2-nitroethylene can be exemplified.

The compounds of the formula (III) as starting materials mean those based on the aforementioned definitions of $R^1$, $R^2$ and Z.

In the formula (III), $R^1$, $R^2$ and Z preferably have the meanings already given above.

The compounds of the formula (III) include in part known compounds [see Nihon Kagaku Zasshi (Periodical of Japanese Chemistry), vol. 83, pages 218–222, 1962, J. Chem. Soc. Perkin I, 1979, pages 2364–2368].

The compounds of the formula (III), for instance, may be prepared in accordance with the method described in the above reference, J. Chem. Soc. Perkin I, 1979, pages 2364–2368.

The compounds of the formula (III), where $R^2$ is hydrogen, can be obtained when compounds of the formula (VII)

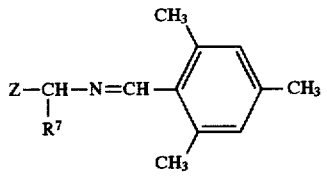

(VII)

wherein $R^7$ and Z have the same meanings as mentioned above, are hydrolyzed.

The compounds of the formula (VII) can be obtained when Schiff-bases of the formula (VIII)

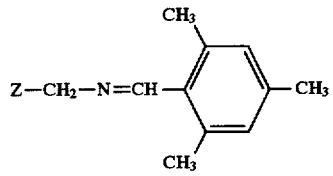

(VIII)

wherein Z has the same meaning as mentioned above, are alkylated by reacting with compounds of the formula (IX)

$$R^7—Hal \qquad (IX)$$

wherein $R^7$ has the same meaning as mentioned above, and Hal is halogen, in the presence of a catalytic amount of butyl-lithium and in the presence of an inert solvent such as tetrahydrofuran.

The compounds of the formula (VIII) can be obtained when compounds of the formula (X)

$$Z—CH_2—NH_2 \qquad (X)$$

wherein Z has the same meaning as mentioned above, are reacted with mesitaldehyde in the presence of inert solvents.

The compounds of the formula (X) include those described in the U.S. Pat. No. 4,499,097, and the aforesaid Nihon Kagaku Zasshi.

In the process b), the compounds of the formula (Ia) as a starting material correspond in part to the compounds of formula (I) which can be prepared by the above process a).

The compounds of the formula (IV) as a starting material mean those based on the aforementioned definitions of $R^5$ and $R^6$.

In the formula (IV), $R^5$ and $R^6$ preferably have the meanings already given above.

The compounds of the formula (IV) are well known in the field of organic chemistry and, as examples, there may be mentioned: methylamine, diethylamine, and the like.

In the process c), the compounds of the formula (V) as a starting material mean those based on the aforementioned definitions of $R^2$ and $R^4$.

In the formula (V), $R^2$ and $R^4$ preferably have the meanings already given above.

The compounds of the formula (V) are known (see e.g. J. Am. Chem. Soc., vol. 76, pages 1877–1879, 1954) and, as examples, there may be mentioned: 3-nitro-2-methylisothiourea, 1,2-dimethyl-3-nitroisothiourea, 1,1,2-trimethyl-3-nitroisothiourea, and the like.

The compounds of the formula (VI) as a starting material mean those based on the aforementioned definitions of $R^1$, Z and Hal.

In the formula (VI), $R^1$ and Z preferably have the meanings already given above, and Hal preferably represents chlorine or bromine.

The compounds of the formula (VI) are known (see Japanese Patent Laid-open Nos. 178981/1986, 178982/1986 or 183271/1986) and, as examples, there may be mentioned: 2-chloro-5-chloromethylpyridine, 2-chloro-5-chloromethylthiazole and so on.

In the process d), the compounds of the formula (Ic) as a starting material correspond in part to the compounds of the formula (I) which can be prepared by the above process c).

The compounds of the formula (IV) are the same as those used in the above process b).

Suitable diluents are all inert solvents. These preferentially include water; aliphatic, cycloaliphatic and aromatic, optionally chlorinated, hydrocarbons, such as hexane, cyclohexane, petroleum ether, ligroin, benzene, toluene, xylene, methylene chloride, chloroform, carbon tetrachloride, ethylene chloride, trichloroethylene, chorobenzene and the like; ethers such as diethyl ether, methyl ethyl ether, di-isopropyl ether, dibutyl ether, propylene oxide, dioxane, tetrahydrofuran and the like; ketones such as acetone, methylethyl ketone, methyl-iso-propyl ketone, methyl-iso-butyl ketone; nitriles such as acetonitrile, propionitrile, acrylonitrile and the like; alcohols such as methanol, ethanol, iso-propanol, butanol, ethylene glycol and the like; esters such as ethyl acetate, amyl acetate; acid amides such as dimethyl formamide, dimethyl acetamide and the like; and sulfones and sulfoxides such as dimethyl sulfoxide, sulfolane and the like; and bases, for example, such as pyridine.

In the above-mentioned process a), the reaction temperature can be varied within a wide range. In general, the reaction is carried out at a temperature of from about 0° C. to 150° C., preferably from about 20° C. to about 90° C.

In general, the reaction is preferably carried out under normal pressure, and also elevated or reduced pressure.

In carrying out the process a), for instance, about 0.9 to slightly above equimolar amounts of the compounds of the formula (III) may be employed per mole of the compounds of the formula (II), and the mixture is reacted in the presence of inert solvents under heat-reflux until the generation of mercaptan ceases, so that the desired compounds of the formula (I) can be obtained.

In carrying out the process b), suitable diluents include the same solvents as exemplified for the process a).

In the above-mentioned process b), the reaction temperature can be varied within a wide range. For example, the reaction is carried out at a temperature in the range of from about 0° C. to about 150° C., preferably from about 20° C. to about 90° C.

In general, the reaction is preferably carried out under normal pressure, and also elevated or reduced pressure.

In carrying out process b), for instance, equimolar to a slight molar excess of the compounds of formula (IV) may be employed per mole of the compounds of the formula (Ia), and the mixture is reacted in the presence of inert solvents, so that the desired compounds of the formula (I) can be obtained.

In carrying out the process c), suitable diluents include the same solvents as exemplified for the process a).

The above-mentioned process c) may be carried out in the presence of acid binders such as, for example, conventionally used hydroxide, hydride, carbonate, bicarbonate and alcolate of alkali metal, tertiary amines such as, for example, triethyl amine, diethyl aniline, pyridine, etc.

In the above-mentioned process c), the reaction temperature can be varied within a wide range. In general, the reaction is carried out at a temperature of from about 0° C. to the boiling point of the reactant mixture, preferably from about 0° C. to about 80° C.

In general, the reaction is preferably carried out under normal pressure, or also elevated or reduced pressure.

In carrying out the process c), for instance, about 1 to 1.2 moles, preferably 1 mole of compound (VI) may be employed per mole of the compounds of the formula (V), and the mixture is reacted in the presence of inert solvents, such as e.g. dimethylsulfoxide, and in the presence of acid binder, such as e.g. sodium hydride, so that the desired compounds of the formula (I) can be obtained.

In carrying out the process d), suitable diluents include the same solvents as exemplified for the process a).

In the above-mentioned process d), the reaction temperature can be varied within a wide range. In general, the reaction is carried out at a temperature in the range of from about 0° C. to about 150° C., preferably from about 20° C. to about 90° C.

In general, the reaction is preferably carried out under normal pressure, or also elevated or reduced pressure.

In carrying out the process d), for instance, equimolar to a slight molar excess of the compounds of formula (IV) may be employed per mole of the compounds of the formula (Ic), and the mixture is reacted in the presence of inert solvents, so that the desired compounds of the formula (I) can be obtained.

The active compounds are well tolerated by plants, have a favorable level of toxicity to warm-blooded animals, and can be used for combating arthropod pests, especially insects which are encountered in agriculture, in forestry, in the protection of stored products and of materials, and in the hygiene field. They are active against normally sensitive and resistant species and against all or some stages of development. The above-mentioned pests include:

from the class of the Isopoda, for example Oniscus Asellus, Armadillidium vulgare and Porcellio scaber;

from the class of the Diplopoda, for example, Blaniulus guttulatus;

from the class of the Chilopoda, for example, Geophilus carpophagus and Scutigera spec.;

from the class of the Symphyla, for example, Scutigerella immaculata;

from the order of the Thysanura, for example, Lepisma saccharina;

from the order of the Collembola, for example, Onychiurus armatus;

from the order of the Orthoptera; for example, Blatta orientalis, Periplaneta americana, Leucophaea maderae, Blattella germanica, Acheta domesticus, Gryllotalpa spp., Locusta migrato ria migratorioides, Melanoplus differentialis and Schistocerca gregaria;

from the order of the Dermaptera, for example, Forficula auricularia;

from the order of the Isoptera, for example, Reticulitermes spp.;

from the order of the Anoplura, for example, Phylloxera vastatrix, Pemphigus spp., Pediculus humanus corporis, Haematopinus spp. and Linognathus spp.;

from the order of the Mallophaga, for example, Trichodectes spp. and Damalinea spp.;

from the order of the Thysanoptera, for example, Hercinothrips femoralis and Thrips tabaci, from the order of the Heteroptera, for example, Eurygaster spp., Dysdercus intermedius, Piesma guadrata, Cimex lectularius, Rhodnius prolixus and Triatoma spp.;

from the order of the Homoptera, for example, Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp. and Psylla spp.;

from the order of the Lepidoptera, for example, Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Spodoptera exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Cacoecia podana, Capua reticulana, Choristoneura fumiferana, Clysia ambiguella, Homona magnanima and Tortrix viridana;

from the order of the Coleoptera, for example, Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis and Costelytra zealandica;

from the order of the Hymenoptera for example, Diprion spp., Hoplocampa spp., Lasius spp., Monomorium pharaonis and Vespa spp.;

from the order of the Diptera, for example, Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae and Tipula paludosa;

from the order of the Siphonaptera, for example, Xenopsylla cheopis and Ceratophyllus spp.;

from the class of the Arachnida, for example, Scorpio maurus and Latrodectus mactans;

from the order of the Aranina, for example Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp. and Tetranychus spp.

The plant-parasitic nematodes include Pratylenchus spp., Radopholus similis, Ditylenchus dipsaci, Tylenchulus semipenetrans, Heterodera spp., Meloidogyne spp., Aphelenchoides spp., Longidorus spp., Xiphinema spp., and Trichodorus spp..

Furthermore, in the field of veterinary medicine, the novel compound of the present invention can effectively be employed for combating a variety of noxious animal-parasitic pests (internal- and external-parasitic pests), e.g., parasitic insects and nematodes. Such animal-parasitic pests may be exemplified as follows:

From the class of insects, e.g., Gastrophilus spp., Stomoxys spp., Tricodectes spp., Rhodius spp., Ctenocephalides canis and the like.

The active compounds can be converted into the customary formulations, such as solutions, emulsions, wettable powders, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 per cent by weight of active compound, preferably from 0.5 to 90 per cent by weight.

The active compounds according to the invention can be present in their commercially available formulations and in the use forms, prepared from these formulations, as a mixture with other active compounds, such as insecticides, baits, sterilising agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agent are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The preparation and use of the active compounds according to the invention can be seen from the following examples.

Preparative Examples

EXAMPLE 1

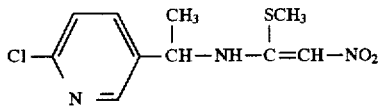

A mixture of 1-(2-chloro-5-pyridyl)ethylamine (4.7 g), 1,1-bis-methylthio-2-nitroethylene (5.0 g) and ethanol (50 ml) was refluxed under heating until the generation of mercaptan ceased. Then, the ethanol was distilled off from the mixture under reduced pressure and the resulting residue was purified on a chromatographic column (the eluent mixture=ethanol+chloroform) to obtain the desired 1-{1-(2-chloro-5-pyridyl)ethylamino}-1-methylthio-2-nitroethylene (3.3 g) having a melting point in the range of from 136° to 140° C.

EXAMPLE 2

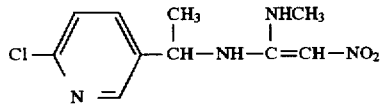

To a solution comprising 1-{1-(2-chloro-5-pyridyl) ethylamino}-1-methylthio-2-nitroethylene (2.7 g) in ethanol (50 ml) was added dropwise an aqueous solution of methylamine (40%, 3 g) at 50° C., followed by a two hours' stirring at the same temperature.

Upon the solution having been cooled to room temperature, the aimed product was separated in the form of crystals, which were filtered and washed with ethanol to obtain the desired 1-{1-(2-chloro-5-pyridyl)ethylamino}-1-methylamino-2-nitroethylene (1.5 g) having a melting point in the range of from 183° to 186° C.

EXAMPLE 3

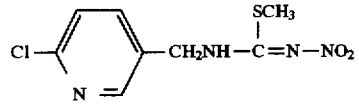

To a solution of 2-methyl-3-nitroisothiourea (15.0 g) in dimethylsulfoxide (100 ml) was gradually added sodium hydride (oil free 2.9 g) at 5° C., while being stirred for one hour. Thereafter, 2-chloro-5-chloromethyl pyridine (18.0 g) was added to the solution at a temperature in the range of from 5° to 10° C., followed by overnight stirring thereof at room temperature. After the dimethylsulfoxide in the solution was distilled off under reduced pressure, the resulting residue was purified on a chromatographic column (the eluent was a mixture of ethanol and chloroform), so as to obtain the desired 1-(2-chloro-5-pyridylmethyl)-2-methyl-3-nitroisothiourea (2.0 g) having a melting point in the range of from 141° to 143° C.

EXAMPLE 4

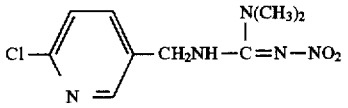

1-(2-chloro-5-pyridylmethyl)-2-methyl-3-nitroisothiourea (1.3 g) was dissolved in ethanol (20 ml) and to the solution was added an aqueous solution (50%) of dimethylamine (0.5 g) at room temperature, followed by one-day stirring at 30° C. The ethanol in the solution was distilled off under reduced pressure and it was purified on a chromatographic column (the eluent was a mixture of methanol and chloroform) so as to obtain the desired 3-(2-chloro-5-pyridylmethyl)-1,1-dimethyl-2-nitroguanidine (1.2 g) having a melting point in the range of from 158° to 160° C.

Background Example 1

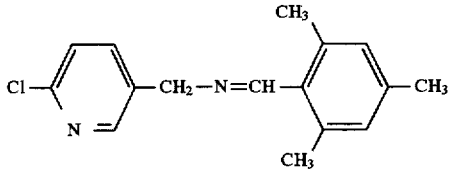

A mixture of 5-aminomethyl-2-chloropyridine (14.25 g), mesitaldehyde (14.8 g) and toluene (100 ml) was heated under reflux for 3 hours. The water which was formed during the reaction was trapped by Dean and Stark constant water separator.

The toluene was distilled off from the mixture under reduced pressure, so as to obtain N-(2,4,6-trimethylbenzylidene)-2-chloro-5-pyridylmethylamine (27 g), m.p. 47°–48° C.

Background Example 2

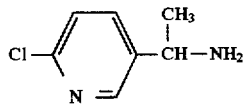

To a stirred solution of N-(2,4,6-trimethylbenzylidene)-2-chloro-5-pyridylmethylamine (10.9 g) in dried tetrahydrofuran (150 ml) cooled to −70° C. under $N_2$ atmosphere was added butyl-lithium (10 w/v % in hexane, 26 ml), causing an immediate intense color to occur. After 30 minutes stirring at the temperature, methyl iodide (5.7 g) was added dropwise, and then the mixture was stirred for three hours without cooling. The solvent was removed under reduced pressure.

To the residue, ethanol (50 ml) and 2N-hydrochloric acid (50 ml) were added and heated under reflux for one hour.

The cooled solution was poured into water (100 ml) and extracted with methylene chloride (50 ml ×2).

The aqueous fraction was neutralized with 2N-sodium hydroxide and extracted with methylene chloride (50 ml ×2). The extract was dried over sodium sulfate and evaporated to obtain 1-(2-chloro-5-pyridyl)ethylamine (4 g). $n_D^{20}$1.5440

Compounds of the formula (I) according to the invention which can be prepared in the same way as in Examples 1 to 4: are set forth in the following Tables 1 and 2.

Where Y is CH in the formula (I), the compounds of the formula (I) are shown in Table 1, and where Y is N in the formula (I), the compounds are shown in Table 2.

TABLE 1

$$Z-\overset{R^1}{\overset{|}{CH}}-\overset{R^2}{\overset{|}{N}}-\overset{R^3}{\overset{|}{C}}=CH-NO_2$$

| Compd. No. | Z | $R^1$ | $R^2$ | $R^3$ | |
|---|---|---|---|---|---|
| 1 | 2-chloro-5-pyridyl | $CH_3$ | H | $SCH_3$ | m.p. 136–140° C. |
| 2 | 2-methyl-5-pyridyl | $C_2H_5$ | H | $SCH_3$ | |
| 3 | 2-bromo-5-pyridyl | $C_2H_5$ | H | $SCH_3$ | |
| 4 | 2-chloro-5-thiazolyl | $CH_3$ | H | $SCH_3$ | |
| 5 | 2-chloro-5-pyridyl | $CH_3$ | $CH_3$ | $NH_2$ | |
| 6 | 2-fluoro-5-pyridyl | $C_3H_7$-n | H | $NH_2$ | |
| 7 | 2-methyl-5-pyridyl | $CH_3$ | H | $NHCH_3$ | |

TABLE 1-continued $$Z-\overset{R^1}{\overset{|}{CH}}-\overset{R^2}{\overset{|}{N}}-\overset{R^3}{\overset{|}{C}}=CH-NO_2$$

| Compd. No. | Z | $R^1$ | $R^2$ | $R^3$ | |
|---|---|---|---|---|---|
| 8 | 2-chloro-5-pyridyl | $CH_3$ | H | $NHCH_3$ | m.p. 183–186° C. |
| 9 | 2-chloro-5-pyridyl | $CH_3$ | H | $N(CH_3)_2$ | m.p. 150–155° C. |
| 10 | 2-chloro-5-pyridyl | $CH_3$ | H | $NH_2$ | |
| 11 | 2-chloro-5-pyridyl | $CH_3$ | $CH_3$ | $NHCH_3$ | |
| 11a | 1.2.3.thiadiazol-5-yl | $CH_3$ | $C_2H_5$ | $SC_3H_7$-n | |

TABLE 2

$$Z-\overset{R^1}{\overset{|}{CH}}-\overset{R^2}{\overset{|}{N}}-\overset{R^3}{\overset{|}{C}}=N-NO_2$$

| Compd. No. | Z | $R^1$ | $R^2$ | $R^3$ | |
|---|---|---|---|---|---|
| 12 | 2-pyridyl | H | H | $SCH_3$ | |
| 13 | 3-pyridyl | H | H | $SCH_3$ | |
| 14 | 4-pyridyl | H | H | $SCH_3$ | |
| 15 | 2-chloro-5-pyridyl | H | H | $SCH_3$ | m.p. 141–143° C. |
| 16 | 2-fluoro-5-pyridyl | $CH_3$ | H | $SCH_3$ | |
| 17 | 2-chloro-5-pyridyl | H | $CH_3$ | $SCH_3$ | |
| 18 | 2-methyl-5-pyridyl | H | H | $SC_2H_5$ | |
| 19 | 2-chloro-5-pyridyl | $CH_3$ | $CH_3$ | $SC_2H_5$ | |
| 20 | 2-bromo-5-pyridyl | H | H | $SC_3H_7$-n | |
| 21 | 2-chloro-5-pyridyl | H | H | $NH_2$ | m.p. 197–199° C. |
| 22 | 2-chloro-5-pyridyl | H | $CH_3$ | $NH_2$ | m.p. 166–168° C. |
| 23 | 2-chloro-5-pyridyl | H | $C_2H_5$ | $NH_2$ | |
| 24 | 2-chloro-5-pyridyl | H | $C_3H_7$-n | $NH_2$ | |
| 25 | 2-chloro-5-pyridyl | $CH_3$ | H | $NH_2$ | $n_D^{20}$ 1.5739 |
| 26 | 2-bromo-5-pyridyl | H | H | $NH_2$ | |
| 27 | 2-chloro-5-thiazolyl | H | H | $NH_2$ | |
| 28 | 2-chloro-5-pyridyl | H | H | $NHCH_3$ | m.p. 151–155° C. |
| 29 | 2-chloro-5-pyridyl | H | $CH_3$ | $NHCH_3$ | m.p. 135–139° C. |
| 30 | 2-chloro-5-pyridyl | H | $C_2H_5$ | $NHCH_3$ | |
| 31 | 2-chloro-5-pyridyl | H | $C_3H_7$-n | $NHCH_3$ | |
| 32 | 2-chloro-5-pyridyl | $CH_3$ | H | $NHCH_3$ | |
| 33 | 2-chloro-5-thiazolyl | H | H | $NHCH_3$ | |
| 34 | 2-chloro-5-thiazolyl | H | $CH_3$ | $NHCH_3$ | |
| 35 | 2-chloro-5-pyridyl | H | H | $NHC_2H_5$ | m.p. 123–127° C. |
| 36 | 2-chloro-5-pyridyl | H | $CH_3$ | $NHC_2H_5$ | |
| 37 | 2-chloro-5-pyridyl | $C_4H_9$-n | $C_2H_5$ | $NHC_2H_5$ | |
| 38 | 2-fluoro-5-pyridyl | H | H | $NHC_2H_5$ | |
| 39 | 2-chloro-5-pyridyl | H | H | $NHC_3H_7$-n | |
| 40 | 2-chloro-5-pyridyl | H | $CH_3$ | $NHC_3H_7$-n | |
| 41 | 2-chloro-5-thiazolyl | H | H | $NHC_3H_7$-n | |
| 42 | 2-chloro-5-pyridyl | H | $C_2H_5$ | $NHC_3H_7$-n | |
| 43 | 2-chloro-5-pyridyl | H | H | $NHC_3H_7$-iso | m.p. 161–165° C. |
| 44 | 2-chloro-5-pyridyl | H | $CH_3$ | $NHC_3H_7$-iso | |

TABLE 2-continued $$Z-\overset{R^1}{\overset{|}{C}}H-\overset{R^2}{\overset{|}{N}}-\overset{R^3}{\overset{|}{C}}=N-NO_2$$

| Compd. No. | Z | $R^1$ | $R^2$ | $R^3$ | |
|---|---|---|---|---|---|
| 45 | 2-chloro-5-pyridyl | H | H | $N(CH_3)_2$ | m.p. 158–160° C. |
| 46 | 2-chloro-5-thiazolyl | H | H | $N(CH_3)_2$ | |
| 47 | 2-chloro-5-thiazolyl | H | $CH_3$ | $N(CH_3)_2$ | |
| 48 | 2-chloro-5-pyridyl | H | $CH_3$ | $N(CH_3)_2$ | m.p. 96–99° C. |
| 49 | 2-chloro-5-pyridyl | H | $C_2H_5$ | $N(CH_3)_2$ | |
| 50 | 2-chloro-5-thiazotyl | $CH_3$ | H | $N(CH_3)_2$ | |
| 51 | 2-chloro-5-pyridyl | H | H | $N-C_2H_5$ \| $CH_3$ | |
| 52 | 2-chloro-5-pyridyl | H | $CH_3$ | $N-C_2H_5$ \| $CH_3$ | |
| 53 | 2-chloro-5-thiazolyl | H | H | $N-C_2H_5$ \| $CH_3$ | |
| 54 | 2-chloro-5-thiazolyl | H | $CH_3$ | $N-C_2H_5$ \| $CH_3$ | |
| 55 | 2-chloro-5-pyridyl | H | H | $N-C_3H_7$-iso \| $CH_3$ | |
| 56 | 2-chloro-5-pyridyl | H | H | $N(C_2H_5)_2$ | |
| 57 | 2-chloro-5-pyridyl | H | $CH_3$ | $N(C_2H_5)_2$ | |
| 58 | 2-chloro-5-pyridyl | H | $C_2H_5$ | $N(C_2H_5)_2$ | |
| 59 | 2-chloro-5-pyridyl | H | $C_4H_9$-n | $NHCH_3$ | |
| 60 | 2-chloro-5-pyridyl | H | H | $NHC_4H_9$-n | |
| 61 | 4-pyridyl | H | $CH_3$ | $NH_2$ | m.p. 153–155° C. |
| 62 | 2-pyridyl | H | $CH_3$ | $NH_2$ | |
| 63 | 3-pyridyl | H | $CH_3$ | $NH_2$ | m.p. 139–141° C. |
| 64 | 4-pyridyl | H | H | $NHCH_3$ | |
| 65 | 4-pyridyl | H | $CH_3$ | $NHCH_3$ | |
| 66 | 3-pyridyl | H | H | $NHCH_3$ | |
| 67 | 3-pyridyl | H | $CH_3$ | $NHCH_3$ | |
| 68 | 2-pyridyl | H | H | $NHCH_3$ | |
| 69 | 2-pyridyl | H | $CH_3$ | $NHCH_3$ | |
| 70 | 4-pyridyl | H | H | $N(CH_3)_2$ | |
| 71 | 3-pyridyl | H | H | $N(CH_3)_2$ | |
| 72 | 2-pyridyl | H | H | $N(CH_3)_2$ | |
| 73 | 2-methyl-5-pyrazinyl | H | $CH_3$ | $NH_2$ | |
| 74 | 2-pyrimidynyl | H | H | $NH_2$ | |
| 75 | 3-methyl-5-isoxazolyl | H | H | $NH_2$ | |
| 76 | 3-methyl-5-isoxazolyl | H | H | $NHCH_3$ | |
| 77 | 3-methyl-5-isoxazolyl | H | H | $N(CH_3)2$ | |

Biological Tests

Comparative compound E-1

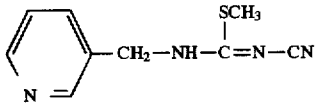

(disclosed in Japanese Patent Laid-open No. 233903/1988)

EXAMPLE 5 (Biological Test)

Test on Nephotettix cincticeps having resistance to organophosphorus agents:

Preparation of a test chemical

Solvent: 3 parts by weight of xylene

Emulsifier: 1 part by weight of polyoxyethylene alkyl phenyl ether

To form a suitable preparation, 1 part by weight of the active compound was mixed with the aforesaid amount of the solvent containing the aforesaid amount of the emulsifier. The mixture was diluted with water to a predetermined concentration.

Testing Method

Onto rice plants, about 10 cm tall, planted in pots each having a diameter of 12 cm was sprayed 10 ml per pot of the water-dilution of each active compound in a predetermined concentration prepared as above. The sprayed chemical was dired, and a wire net having a diameter of 7 cm and a height of 14 cm was put over each pot, and 30 female imagoes of Nephotettix cincticeps showing resistance to organophosphorus agents were released into the net. The pots were each placed in a constant temperature chamber and the number of dead insects was examined 2 days later, and the Insect mortality was calculated.

The results are shown in Table 3.

TABLE 3

| Compound No. | Concentration of the active component, ppm | Insect mortality, % |
|---|---|---|
| 8 | 8 | 100 |
| 9 | 8 | 100 |
| 22 | 8 | 100 |
| 45 | 8 | 100 |
| Control | | |
| E-1 | 50 | 0 |

EXAMPLE 6 (Biological Test)

Test on planthoppers:

Testing method

A water dilution in a predetermined concentration of the active compound prepared as in Example 5 was sprayed onto rice plants, about 10 cm tall, grown in pots with a diameter of 12 cm in an amount of 10 ml per pot. The sprayed chemical was dried, and a wire net, 7 cm in diameter and 14 cm tall, was put over each of the pots. Thirty female imagoes of Nilaparvata lugens Stal of a strain which showed resistance to organophosphorus chemicals were released into the net. The pots were left to stand in a constant temperature chamber and the number of dead insects was examined two days later. The kill ratio was then calculated.

In the same way as above, the insect mortality was calculated on Sogatella furcifera Horvath and organophosphorus-resistant Laodelphax striatellus Fallen.

The results are shown in Table 4.

TABLE 4

| Compound No. | Concentration of the active component, ppm | Insect mortality, % | | |
|---|---|---|---|---|
| | | *Nilaparvata lugens* | *Laodelphax striatellus* | *Sogatella furcifera* |
| 8 | 8 | 100 | 100 | 100 |
| 9 | 8 | 100 | 100 | 100 |
| 22 | 8 | 100 | 100 | 100 |
| 45 | 8 | 100 | 100 | 100 |
| Control | | | | |
| E-1 | 50 | 0 | 0 | 0 |

It is understood that the specification and examples are illustrative but not limitative of the present invention and that other embodiments within the spirit and scope of the invention will suggest themselves to those skilled in the art.

We claim:

1. A [novel] nitro compound of the formula

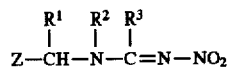

wherein $R^1$ and $R^2$ are hydrogen or $C_{1-4}$ alkyl, $R^3$ is —S—$R^4$ or

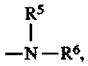

$R^4$ is $C_{1-4}$ alkyl, $R^5$ and $R^6$ are hydrogen or $C_{1-4}$ alkyl, and

Z is [pyridyl,] thiazolyl, thiadiazolyl, pyrimidinyl, or isoxazolyl which may be substituted by halogen or $C_{1-4}$-alkyl.

2. A compound according to claim 1, wherein $R^1$ and $R^2$ are hydrogen or methyl, $R^3$ is —S—$R^4$ or

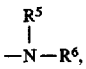

$R^4$ is methyl, $R^5$ and $R^6$ are hydrogen or methyl, and

Z is [pyridyl,] thiazolyl, thiadiazolyl, pyrimidinyl, or isoxazolyl which may be substituted by chlorine or methyl.

3. A compound according to claim 1, wherein $R^1$ and $R^2$ are hydrogen or methyl, $R^3$ is

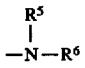

in which $R^5$ and $R^6$ are hydrogen or methyl, and

Z is [2-chloro-5-pyridyl or] 2-chloro-5-thiazolyl.

4. A compound according to claim 1, wherein $R^1$ and $R^2$ are hydrogen or methyl, $R^3$ is

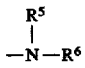

in which $R^5$ and $R^6$ are hydrogen or methyl, and

Z is [2-chloro-5-pyridyl or] 2-chloro-5-thiazolyl.

5. A compound according to claim [1] *15*, wherein $R^1$ and $R^2$ are hydrogen or methyl, $R^3$ is

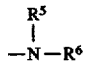

in which $R^5$ and $R^6$ are hydrogen or methyl,

[Y is N,] and

Z is 2-chloro-5-pyridyl.

6. A compound according to claim [1] *15*, wherein such compound is 3-(2-chloro-5-pyridylmethyl)-1-methyl-2-nitroguanidine of the formula

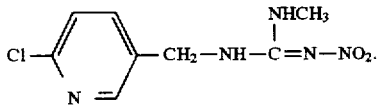

7. A compound according to claim [1] *15*, wherein such compound is 3-(2-chloro-5-pyridylmethyl)-1,1-dimethyl-2-nitroguanidine of the formula

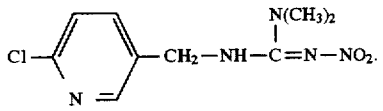

8. A compound according to claim [1] *15*, wherein such compound is 3-(2-chloro-5-pyridylmethyl)-1,3-dimethyl-2-nitroguanidine of the formula

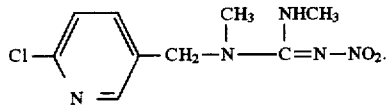

9. A compound according to claim [1] *15*, wherein such compound is 3-(2-chloro-5-pyridymethyl)-1,1,3-trimethyl-2-nitroguanidine of the formula

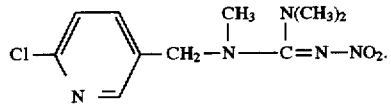

10. A compound according to claim [1] *15*, wherein such compound is 3-(2-chloro-5-pyridylmethyl)-3-methyl-2-nitroguanidine of the formula

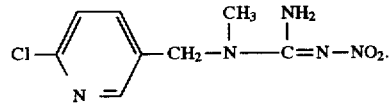

[11. A compound according to claim 1, wherein such compound is 3-(2-chloro-5-thiazolylmethyl)-1-methyl-2-nitroguanidine of the formula

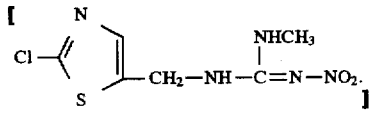

12. An insecticidal composition comprising an insecticidally effective amount of a compound according to claim 1 and a diluent.

13. A method of combating insects which comprises applying to such insects or to a locus from which it is desired to exclude such insects an insecticidally effective amount of a compound according to claim 1 and a diluent.

14. The method according to claim 13, wherein such compound is

[3-(2-chloro-5-pyridylmethyl)-1-methyl-2-nitroguanidine;
3-(2-chloro-5-pyridylmethyl)-1,1-dimethyl-2-nitroguanidine;
3-(2-chloro-5-pyridylmethyl)-1,3-dimethyl-2-nitroguanidine;
3-(2-chloro-5-pyridylmethyl)-1,1,3-trimethyl-2-nitroguanidine;
3-(2-chloro-5-pyridylmethyl)-3-methyl-2-nitroguanidine; or]
3-(2-chloro-5-thiazolylmethyl)-1-methyl-2-nitroguanidine.

*15. A nitro compound of the formula*

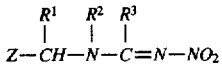

*wherein*

*$R^1$ and $R^2$ are hydrogen or $C_{1-4}$-alkyl,*

*$R^3$ is —S—$R^4$ or*

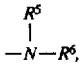

*$R^4$ represents $C_{1-4}$-alkyl,*

*$R^5$ and $R^6$ represent hydrogen or $C_{1-4}$-alkyl, and*

*Z is pyridyl substituted by chlorine or methyl.*

*16. A compound according to claim 15, wherein*

*$R^1$ and $R^2$ are hydrogen or methyl,*

*$R^3$ is*

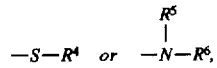

*$R^4$ is methyl,*

*$R^5$ and $R^6$ are hydrogen or methyl, and*

*Z is pyridyl substituted by chlorine or methyl.*

*17. A compound according to claim 15, wherein*

*$R^1$ and $R^2$ are hydrogen or methyl,*

*$R^3$ is*

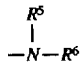

*in which $R^5$ and $R^6$ are hydrogen or methyl, and*

*Z is 2-chloro-5-pyridyl.*

*18. An insecticidal composition comprising an insecticidally effective amount of a compound according to claim 15 and a diluent.*

*19. A method of combating insects which comprises applying to such insects or to a locus from which it is desired to exclude such insects an insecticidally effective amount of a compound of the formula*

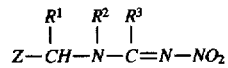

*wherein*

*$R^1$ and $R^2$ are hydrogen or $C_{1-4}$-alkyl,*

*$R^3$ is —S—$R^4$ or*

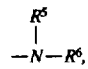

*$R^4$ represents $C_{1-4}$-alkyl,*

*$R^5$ and $R^6$ represent hydrogen or $C_{1-4}$-alkyl, and*

*Z is pyridyl substituted by chlorine or methyl,*

*in admixture with a diluent.*

*20. The method according to claim 19, wherein such compound is*

*3-(2-chloro-5-pyridylmethyl)-1-methyl-2-nitroguanidine;*

*3-(2-chloro-5-pyridylmethyl)-1,1-dimethyl-2-nitroguanidine;*

*3-(2-chloro-5-pyridylmethyl)-1,3-dimethyl-2-nitroguanidine;*

*3-(2-chloro-5-pyridylmethyl)-1,1,3-trimethyl-2-nitroguanidine; or*

*3-(2-chloro-5-pyridylmethyl)-3-methyl-2-nitroguanidine.*

* * * * *